US005522708A

United States Patent [19]
Nimberger

[11] Patent Number: 5,522,708
[45] Date of Patent: Jun. 4, 1996

[54] FLUID SAMPLING PUMP WITH ADJUSTABLE VALVE MEANS AND EASILY ACCESSABLE FILTER

[75] Inventor: Spencer M. Nimberger, Houston, Tex.

[73] Assignee: PGI International, Ltd., Houston, Tex.

[21] Appl. No.: 373,883

[22] Filed: Jan. 17, 1995

Related U.S. Application Data

[63] Continuation of Ser. No. 33,567, Mar. 18, 1993, abandoned.

[51] Int. Cl.$^6$ .............................. F04B 53/10; F04B 53/20
[52] U.S. Cl. .................. 417/313; 417/440; 417/506; 73/863.84
[58] Field of Search .................. 417/400, 401, 417/402, 440, 313, 454, 506, 569; 92/13.41, 13.6; 137/540; 73/864.34, 863.83, 863.84

[56] References Cited

U.S. PATENT DOCUMENTS

| | | | |
|---|---|---|---|
| 1,199,526 | 9/1916 | Bowser | 92/13.6 |
| 3,156,160 | 11/1964 | Meyer et al. | 92/13.6 |
| 4,093,406 | 6/1978 | Miller | 417/401 |
| 4,276,001 | 6/1981 | Holmes | 417/401 |
| 4,531,895 | 7/1985 | Zeck | 417/401 |
| 4,565,504 | 1/1986 | George et al. | 417/401 |
| 4,628,750 | 12/1986 | Welker | 73/864.63 |
| 4,928,536 | 5/1990 | Welker | 73/863.83 |
| 5,000,077 | 3/1991 | Habicht | 92/13.6 |
| 5,032,063 | 7/1991 | Zeck et al. | 417/383 |
| 5,074,154 | 12/1991 | Allen et al. | 73/864.34 |
| 5,092,742 | 3/1992 | Allen et al. | 417/401 |
| 5,152,678 | 10/1992 | Zeck | 417/401 |
| 5,191,801 | 3/1993 | Allen et al. | 73/864.34 |
| 5,213,586 | 5/1993 | Welker | 417/401 |

FOREIGN PATENT DOCUMENTS

| | | | |
|---|---|---|---|
| 862073 | 7/1949 | Germany | 417/313 |

*Primary Examiner*—Richard A. Bertsch
*Assistant Examiner*—Roland G. McAndrews, Jr.
*Attorney, Agent, or Firm*—Browning, Bushman, Anderson & Brookhart

[57] ABSTRACT

An improved sampling pump has utility for withdrawing contaminated fluid from a low pressure source and outputting cleaned fluid to a sampling container. The fluid pump assembly of the present invention includes an operator unit for reciprocating plunger, and a side body port positioned within the pump body for receiving a removable filter. The pump assembly includes a discharge check valve which is ideally positioned within the pump body for minimizing "dead areas" within the pump, but is also adjustable for controlling the downstream pressure generated by the pump. An operator unit for the pumping assembly may include a spacer attached to the operator piston for selectively controlling the pump stroke. The pump assembly preferably has a pump body inlet port substantially aligned with the plunger axis. High pump reliability is obtained by the preferred filtering technique which cleans both the fluid supplied to the pump and the fluid supplied to the operator unit.

18 Claims, 3 Drawing Sheets

FLUID SAMPLING PUMP WITH ADJUSTABLE VALVE MEANS AND EASILY ACCESSABLE FILTER

This is a continuation of U.S. application Ser. No. 08/033,567, filed on Mar. 18, 1993, now abandoned.

FIELD OF THE INVENTION

The present invention relates to pumps which periodically withdraw fluid from a low pressure source and pass the fluid to a downstream container or other device. More particularly, the present invention relates to a relatively low cost pump ideally suited for periodically withdrawing contaminated gas from a low pressure line, and outputting the gas to a sampling container, with the pump operator being powered by the low pressure source.

BACKGROUND OF THE INVENTION

Various situations arise wherein one seeks to pump a liquid or gas from a low pressure source, such as a flow line, and output the fluid to a downstream container, such as a sample bottle. The sample bottle may be periodically sent to a laboratory for analysis to determine the BTU content of the sampled fluid, and thereby determine the BTU content of the gas flowing in the low pressure line. In many situations, a separate power source, such as an electric pump or pressurized hydraulic line, is readily available for driving the pump. In other situations typified by remote applications, a separate power source is not readily available or is not cost-effective for driving or powering the pump. In these latter situations, the low pressure source can be used to drive the pump, thereby avoiding the expenses associated with a separate power supply. Sampling pumps have typically been powered by an operator unit which receives low pressure from the downstream source, and which uses the low pressure as the driving force. Examples of sampling pumps which may utilize the downstream pressurized line as the driving force for the pump operator are disclosed in U.S. Pat. Nos. 4,928,536 and 5,032,063.

Many of the advantages of a sampling pump powered by an upstream fluid pressure frequently are not realized if the upstream fluid is contaminated with particles, such as rust, scale, or other particulate. The fluid ideally is filtered before entering the pump to reduce maintenance costs, and this filter ideally is closely adjacent the pump inlet port check valve. If the fluid line to the pump operator unit is not also filtered, however, service costs for the operator unit can become excessive. Service personnel periodically change the pump inlet filter, and may not inspect or change the operator unit filter.

In some applications, the pump inlet filter may be cleaned by the lower pressure fluid itself, as disclosed in U.S. Pat. No. 5,074,154. Much of the fluid flowing to a sampling pump may thus pass by, rather than through, the pump inlet filter in a "hot loop", thereby continually cleaning the pump inlet filter. In other applications, this hot loop technique is not feasible, and substantially all fluid flow to the pump is input and discharged from the pump.

In many applications, a check valve may be provided within the flow line downstream from the sampling pump, and in these cases an adjustable check valve may be utilized to control the downstream fluid pressure. An adjustable check valve offers a significant advantage in that the combination of (1) downstream fluid pressure desired as a result of the pumping operation, and (2) the efficiency of the pumping operations, may be maximized by using this check valve to adjust the downstream pressure. When used for gas applications, however, the pump discharge check valve ideally is closely adjacent the pump plunger, thereby minimizing the "dead areas" within the pumping system and improving pump efficiency, as disclosed in U.S. Pat. No. 5,074,154.

Various techniques have been employed to adjust the pumping capacity, i.e., the volume of each pump stroke. The '154 patent referenced above, for example, discloses a micrometer for adjusting the stroke of the operator piston, and thus the pumping plunger and thus the volume of the pump stroke. Also, it is well known to provide a purge system for a pump, so that fluid from the pump inlet may periodically effectively bypass the pump and go directly to the pump outlet, as disclosed in U.S. Pat. Nos. 4,440,032, and 5,074,154. Improved techniques are required, however, to provide a downstream fluid pressure pump with a lower cost pump stroke adjustment, and to reduce the expense associated with providing an improved pump with a purge system.

The disadvantages of the prior art are overcome by the present invention, and a novel pump is hereinafter disclosed to satisfy the need for a low cost and reliable pump which may be used for various applications.

SUMMARY OF THE INVENTION

The sampling pump of the present invention, in a preferred embodiment, utilizes a pump operator unit comprising a piston responsive to upstream fluid pressure to drive the operator and therefore stroke the pump plunger, so that a separate pump power source is not required to perform this function. The pump stroke may be easily and inexpensively rendered adjustable by providing an attachment member secured to the operator piston, so that a spacer, which has a top surface a selected distance from the top face of the operator unit piston, can be removable secured to the attachment member.

The pump includes a filter positioned in a side body port of the pump body by a removable plug, so that the plug and filter may be periodically removed, the filter cleaned, and the filter and plug reinstalled without disassembling the pump from the upstream low pressure source or the downstream high pressure source. The filter is provided between the pump body inlet and the pump inlet check valve, and an actuation line to the pump actuator has its actuator line inlet between the filter and the pump inlet check valve. All fluids passing to either the pumping chamber or to the pump operator are thus filtered to enhance the life of the pump assembly.

The pump outlet check valve engages a seat within the body of the pump, so that dead areas within the pump are minimized. The check valve is, however, adjustable to control downstream fluid pressure. In one embodiment, the pump discharge check valve is rendered adjustable by selecting a check valve stud with a pocket having a selected depth for receiving a biasing spring, so that the biasing force of the spring may be easily altered. In another embodiment, the check valve is rendered adjustable for rotating an adjustment screw provided within a sleeve member interconnected with the pump body, and a resealable end cap allows the operator to easily obtain access to the adjustment screw. A purge line is provided within the pump body for interconnecting the pump inlet port and the pump outlet port, and fluid flow through this line may be controlled by a purge valve member having its seat also within the pump body. The purge valve is ideally positioned opposite the adjustable check valve with respect to the central axis of the pump, and the pump body outlet port is positioned circumferentially between the purge valve and the check valve. An actuator line port is also positioned circumferentially between the purge valve and the check valve, but is opposite the pump body outlet port with respect to the pump centerline.

It is an object of the present invention to provide an improved low-cost sampling pump with a filter which may be replaced without disassembling the pump from either its upstream or downstream lines.

Another object of the present invention is a sampling pump with an adjustable pump outlet check valve which may be regulated to control downstream pressure, yet positioned within the pump body to minimize dead volumes within the pump.

Yet another object of this invention is to provide a low cost sampling pump with an output check valve and purge valve being positioned opposite the pump centerline, and each of an output port and actuator line port being circumferentially positioned between these valves and opposite each other.

Yet another object of this invention is to provide a low cost sampling pump which includes an upstream fluid-responsive operator unit which may be easily adjusted to regulate the pumping stroke.

It is a feature of this invention that a low cost sampling pump uses the same filter to clean both the fluid entering the pumping chamber and the fluid passed to the operator unit for driving the pump. This filter may be quickly and easily replaced through a side port in the pump body, thereby reducing pump maintenance.

It is another feature of this invention that the pump body includes a purge line for interconnecting the fluid inlet with the fluid outlet and bypassing the pumping chamber, with the purge line being controlled by a valve having its closure member and seat within the pump body.

Yet another feature of the invention is a low cost gas sampling pump with an adjustable output check valve incorporated into the pump body.

An advantage of this invention is that the same sampling pump has a wide number of applications, thereby reducing the overall cost of the pump. The pump of this invention is particularly well suited for withdrawing hydrocarbons from a low pressure gathering line connected to a hydrocarbon well, and discharging the hydrocarbons to a sample container.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
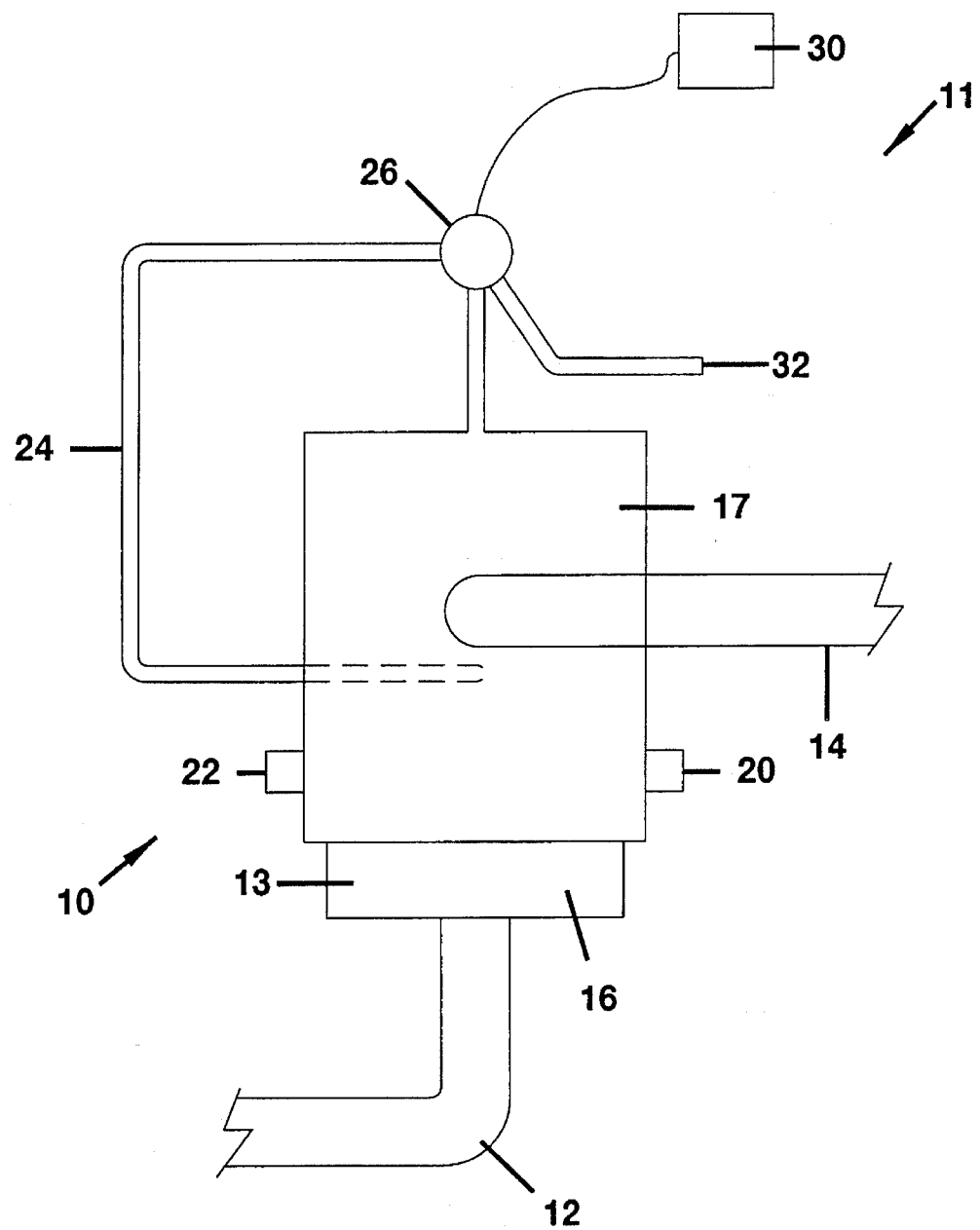
FIG. 1 is a simplistic view of the pump according to the present invention for receiving contaminated fluid from the low pressure source, and for outputting cleaned fluid to a sampling container.

FIG. 1 is a simplistic representation of a pumping assembly 11 according to the present invention for receiving low pressure contaminated fluid from the flow line, container, or other source 12, and outputting a cleaned high pressure fluid to a sampling container, with the sampled fluid passing to the container through output line 14. In an exemplary application, the assembly of the present invention may be used for sampling hydrocarbon gas from various hydrocarbon gathering wells, with the gas being contaminated with scale, debris, or other particulate, and for collecting the sampled hydrocarbon gas in a sampling container. For exemplary purposes, a line 12 may be at approximately 5 psi, while the line 14 and the sampling container may have an initial pressure of 5 psi, and a final pressure of 25 psi just prior to removing the sampling container from the pump for testing. Also, it should be understood that pump assembly pump 10 of the present invention may be used with any number of different flow lines or sources depending on the application, and accordingly in another situation line 12 may be a liquid flow line, and the output from the pump assembly pump 10 may be a storage vessel, such as a tank.

Still referring to FIG. 1, the overall pumping assembly 11 comprises a pump 10 having a body 13 including inlet housing 16 and pump actuator housing 18. Adjustable pump output check valve 20 is simplistically shown for controlling the output pressure to line 14, and a purge valve 22 is also simplistically shown for selectively interconnecting the low pressure line 12 with the output line 14, and thereby purging the pump assembly in a conventional manner. FIG. 1 also shows a solenoid valve 26 in the line 24 for controlling fluid flow to the actuator unit 17. Solenoid 26 may be activated by control 30, which may be in the form on an adjustable timer which intermittently sends an activation signal to valve 26 to briefly open the valve and thereby cause a pump driving stroke. As explained in greater detail subsequently, the pressure from line 12 is thus used as the power source to drive the actuator unit 17 and thus the pump assembly pump 10 during the compression stroke of the pump. During the expansion stroke of the pump, fluid within the actuator unit 17 is prevented by valve 26 from flowing back to the pump inlet housing 16 through line 24, and instead is vented to atmosphere or piped to a safe vent location through exhaust line 32.

Figure 2:
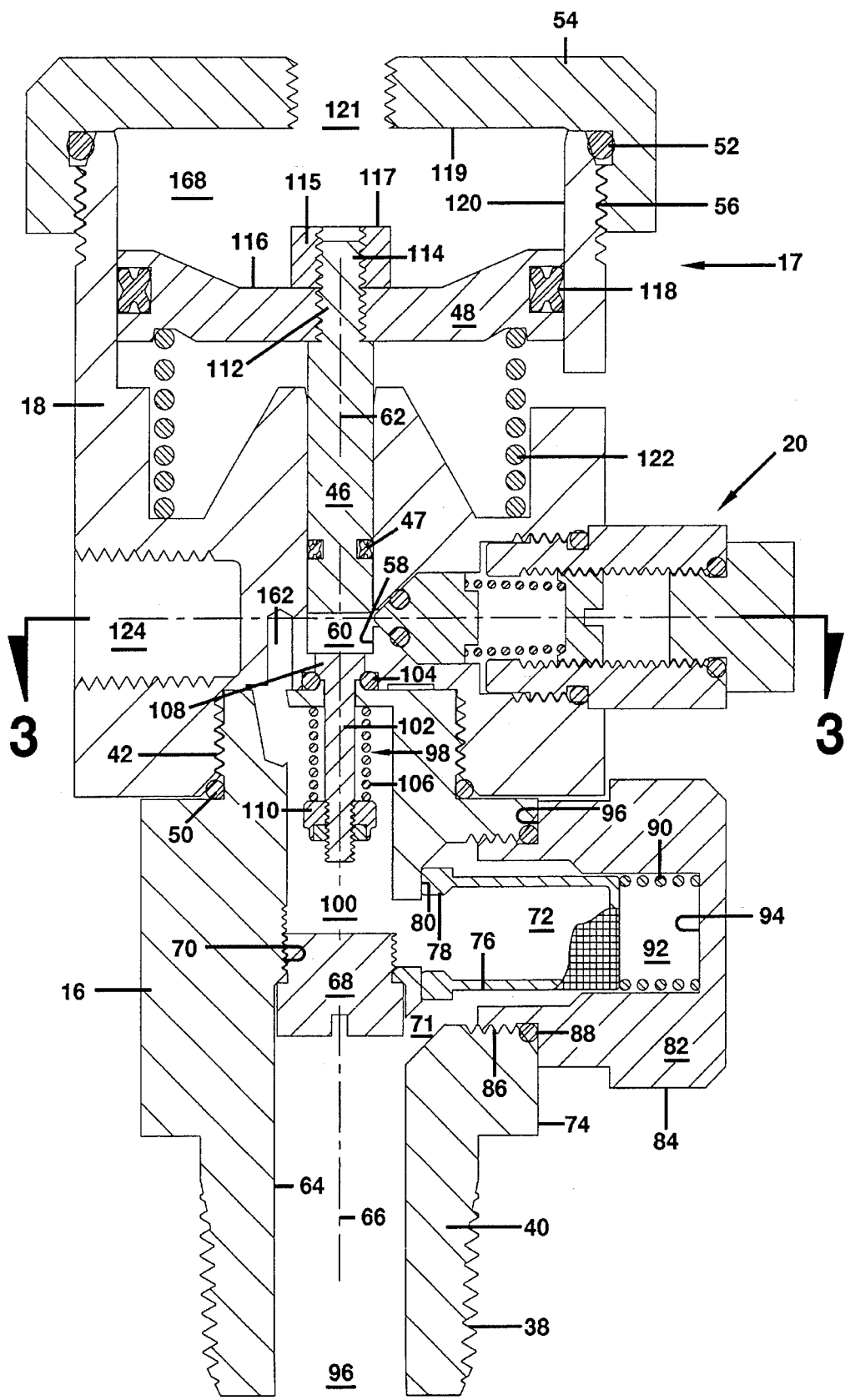
FIG. 2 is a right-angle cross-sectional view an exemplary pump according to the present invention.

FIG. 2 depicts in greater detail the pump inlet housing 16 and the actuator housing 18 generally shown in FIG. 1. The pump inlet housing 16 has tapered threads 38 at the lower end thereof for sealing engagement with corresponding threads at the end of line 12. The lower housing 16 is threaded at 42 to an actuator housing 18, which serves as the housing for both the pump plunger 46 and the operator piston 48. A conventional static O-ring seal 50 provides a fluid-tight seal between the mated housings 16 and 18. A similar seal 52 is provided between the upper end of the housing 18 and the actuator cap 54 threaded to the housing at threads 56. Adjustable outlet check valve 20 generally shown in FIG. 1 is depicted in detail in FIG. 3, and will be described subsequently.

The cylindrical plunger 46 is continually in sealed engagement with bore side walls 58, so that a pumping chamber 60 is formed within the housing 18, with this chamber having a volume determined as a function of the position of the plunger 46 with respect to the housing 18. Plunger 46 is reciprocated by the actuator unit along axis 62, and moves toward actuator cover 54 during its expansion stroke to draw fluid into the chamber 60 from the low pressure line 12, and toward the housing 18 during its compression stroke to expel fluid under high pressure to line 14. A bore 64 within the housing 16 has its inlet axis 66 substantially aligned with the axis 62, and serves to receive fluid from the line 12. A diverter member 68 is threaded at 70 to the housing 16, and is positioned along the inlet axis 66 to cause fluid to divert through the connecting passageway 71 to the side port 72 which is formed in the wall of the housing 16 and extends to an outer surface 74 of the housing. A cup-shaped filter 76 is positioned within the bore 72, with the circular filter end 78 engaging the planar surface 80 formed by the housing 16. The filter 76 is held in place by end cap 82, which may be provided with a hexagonal outer surface 84 for thereby connecting and thereby disconnecting the threads 86 between the end cap and the housing 16. A static O-ring 88 forms a fluid-tight seal between cap 82 and the housing 16. A spring or other biasing member 90 is provided within the pocket 92 within the end cap 84. The pocket 92 has a base surface 94 intentionally spaced a selected distance from the end cap stop surface 96 which engages the surface 74 of the housing 16 to allow the spring 90 to hold the filter 76 in the depicted position. As shown in FIG. 2, the combination of the diverter 68 and the end cap 82 thus causes all fluid which enters pump body through inlet 96 to first pass through the walls of the filter 76 before entering the chamber 100, so that scale, particles, and other debris can be removed by the filter 76. It should also be understood that the filter 76 may be removed, cleaned, and then replaced by unthreading the cap 82, removing the filter 76 from the side port 72 in the housing 16, then reversing the operation to re-install the filter and the end cap.

An inlet check valve assembly 98 controls flow of fluid from the chamber 100 downstream of the filter 76 to the pumping chamber 60, and more particularly prevents flow of fluid from the chamber 60 back to the chamber 100 during the pump compression stroke. The inlet check valve assembly includes a valve member 102 which is biased into sealed engagement with O-ring seal 104 by spring 106, so that seal 104 forms a seal between the head 108 and the housing 16 during the compression stroke of the pump. During the pump expansion stroke, the head 108 moves upward toward the actuator unit 17, thereby compressing the spring 106 positioned about valve member 102. The lower end of the spring may be supported by nut 110. If desired, the position of the nut 110 relative to the head 108 may be adjusted to change the biasing force of the spring 106, and thereby change the required pressure in the chamber 100 which must be obtained before the check valve 98 opens to allow fluid to pass into the pumping chamber 60.

The plunger 46 is sealed by a sealing ring 47, such as a quad ring, for sealing engagement with the side walls 58 of the bore or pumping chamber 60. A threaded stud 112 provided at the upper end of the plunger 46 provides sealed engagement with the piston body 48, and this sealing may be obtained by using an appropriate pipe dope or other locking material. The upper portion 114 of stud 112 extends above the upper face 116 of the piston 48, and serves as an attachment member discussed subsequently. Seal 118 provides dynamic sealing engagement between the cylindrical wall 120 of the housing 18 and the piston 48, and spring 122 biases the piston 48 upward. The actuator unit cover 54 includes a threaded port 121 for mated engagement with solenoid valve 26 at the end of line 24, as shown in FIG. 1.

A spacer 115 is removably securable by threads to attachment member 114. The top surface 117 of spacer 115 engages the lower surface 119 of cover 54, and thereby limits the maximum possible travel of piston 46. By utilizing a spacer 115 selected with a preferred spacing along axis 62 between top surface 117 and upper piston face 116, the maximum stroke of the plunger 46 may thus be easily and inexpensively controlled. If a pumping cycle with a shorter stroke (and thus less maximum volume of chamber 60) is preferred, the cover 54 may be removed and the previous spacer replaced with a new spacer for achieving the desired spacing, then the cover 54 reinstalled.

Figure 3:
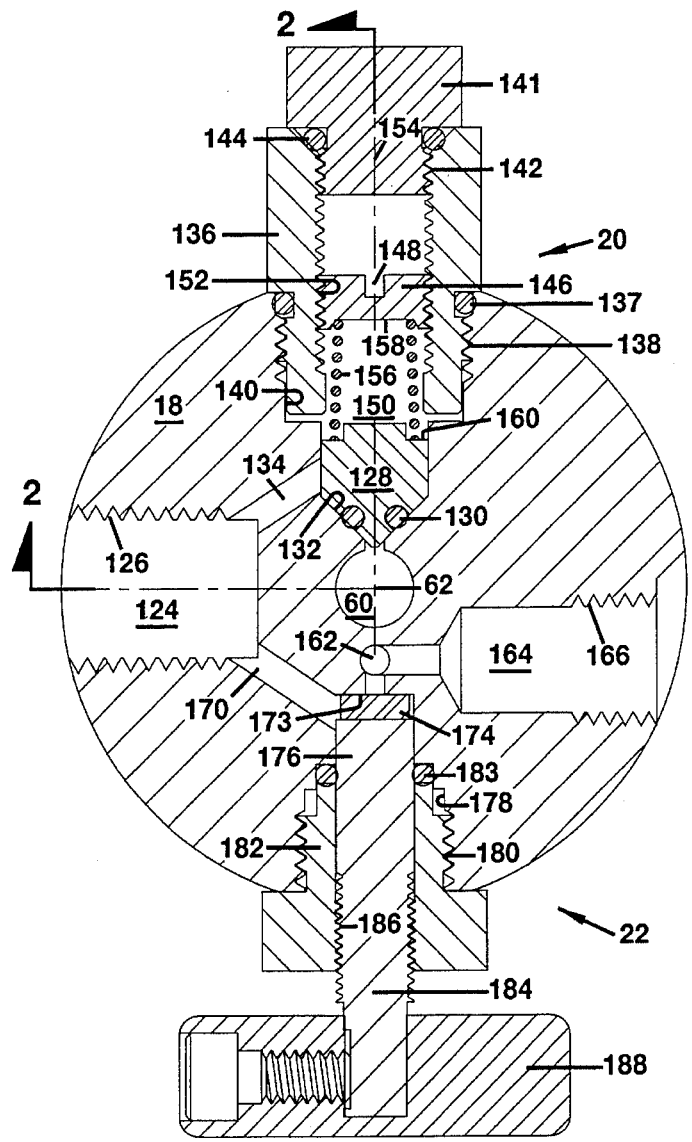
FIG. 3 is a cross-sectional view taken along lines 3—3 in FIG. 2.

FIG. 2 is a right angle cross-sectional view of the pump and actuator, with intersecting planes forming a line aligned with the pump body central axis 62 (section 2—2 in FIG. 3). FIG. 3 is a cross-sectional view taken along lines 3—3 of FIG. 2, accordingly the FIG. 2 view is taken through the center of the outlet check valve adjustment assembly 20, and then through the center of the outlet port 124 which is shown in both FIG. 2 and 3. Port 124 includes tapered threads 126 formed about axis 125 for mated engagement with corresponding threads at the pump end of the line 14. During the compression stroke of the plunger 46, the high pressure fluid unseats the valve member 128 carrying O-ring seal 130 from the seat 132 formed on the housing 18, so that pressurized fluid flows via passage 134 to the pump outlet port 124, and then through the outlet line 14.

Adjustable outlet check valve assembly 20 comprises a sleeve-shaped body 136, which may be threaded at 138 for engagement with mating threads provided in a side port 140 in the housing 18, with the side port extending into fluid communication with the compression chamber 60 as shown in FIG. 3. An end cap 141 includes threads 142 for mating engagement with the sleeve 136, and static seal 144 provides fluid-tight sealing engagement between the resealable end cap 140 and sleeve 136. An adjustment screw 146 including a screwdriver slot 148 is positioned within the interior bore 150 of the sleeve 136. Mating threads 152 thus allow for axial positioning of the adjustment member 146 with respect to the sleeve 136 along the outlet check valve centerline 154. Spring 156 is sandwiched between the end 158 of the adjustment member 146 and the end 160 of the valve member 128 to bias the valve member into sealing engagement with the seat 132. It should be understood that by merely removing the end cap 140, a service technician may use a screwdriver to change the axial spacing between the seat 132 and the adjustment member 146, and thereby selectively control the biasing force of the spring 156 and thus the pressure which must be obtained to overcome the check valve assembly 20 to pass high pressure fluid to the pump outlet port 124.

In reference to FIGS. 2 and 3, it may be seen that passageway 162 in the body 18 provides fluid communication between the actuator line port 164 shown in FIG. 3 and the chamber 100 upstream frown the inlet check valve assembly 98. Filtered low pressure fluid may thus pass through passageway 162 to the port 164, which includes tapered threads 166 for sealing engagement with the line 24 shown in FIG. 1. Cleaned fluid is thus available for passing through the port 12 1 in the cover 54 to fill the chamber 168 above the piston 48, and force the piston and thus the plunger 46 downward during the pump compression stroke. Those skilled in the art will understand that substantially higher output pressure compared to pump inlet pressure is obtained due to the substantially large cross-sectional sealing area of the piston 48 compared to the substantially small cross-sectional sealing area of the plunger 46.

FIG. 3 also depicts passageway 170 connecting the fluid output port 124 with the actuator line port 164. The passageway 170 is normally blocked, however, by a closed purge valve assembly 22 which includes an elastomeric seat 174 for sealing engagement between the sealing surface 173 on the housing 18 and the valve member 176 of the purge valve 22. Purge valve 22 is fitted within a side port 178 in the housing 18, with mating threads 180 between the sleeve 182 and the housing 18 providing a desired mechanical connection, and an O-ring seal 183 providing a fluid-tight connection between the valve member 176 and both the housing 18 and the sleeve 182. The valve stem 184 has threads 186 for engagement with mating threads on the sleeve 182, and accordingly rotation of handle 188 will open or close the valve member 22 in a conventional manner. During normal use of the pump, the valve 22 remains closed, and fluid is supplied to the actuator unit 17 though line 24. The valve 26 as shown in FIG. 1 is opened to pass fluid from the passageway 162 to the port 164, and then through the line 24. In order to purge the pump, valve 22 may be opened, so that low pressure fluid may flow directly from the pump body inlet port 96 through the filter 76, to the chamber 100 and then to the outlet port 124.

FIGS. 2 and 3 also depict a significant feature of the pump according to the present invention which concerns the positioning of the valves and port within the pump body or housing. With reference to FIG. 2, "dead areas" within the pump are minimized by mounting the seal 47 on the plunger 46 to seal between the plunger 46 and pump housing 18, rather than mounting this seal on the housing 18, and also positioning the adjustable check valve 20 as close as reasonably possible to the inlet check seal 104. With reference to FIG. 3, the purge valve 22 is mounted on the pump body in a position opposite the check valve 20 with respect to the central axis 62 of the plunger and thus the central axis of the purging chamber 64 and thus the pump itself. The pump body outlet port is positioned circumferentially between the purge valve 22 and the check valve 20, as shown in FIG. 3. The actuator line port is also positioned circumferentially between the purge valve and the check valve, but is opposite the pump body outlet port with respect to the pump centerline. Thus the valves 20 and 22 are preferably generally opposite each other, and ideally 180° opposite each other, with respect to the centerline of the pump, and a first one of the ports 124, 164 is positioned circumferentially between these valves, while the other of these ports is also positioned circumferentially between these valves, but is opposite the first port with respect to the pump centerline. This design results in a compact arrangement that is ideally suited for achieving the purposes of the present invention.

Figure 4:
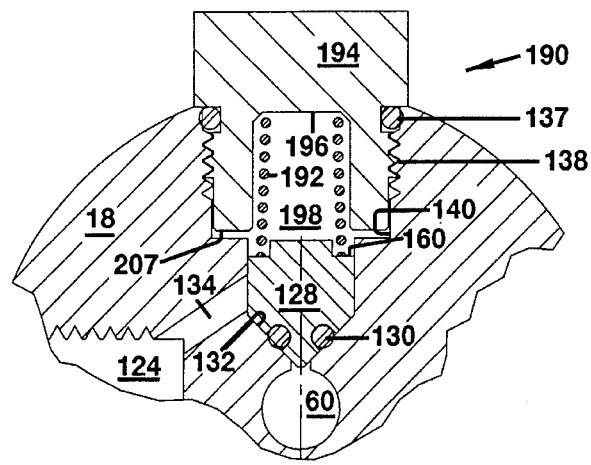
FIG. 4 depicts an alternate embodiment of an adjustable outlet check valve positioned within a portion of the pump body as shown in FIG. 3.

FIG. 4 depicts one modification for the adjustable outlet check valve assembly 20 described above. The pump outlet check valve assembly 190 thus replaces assembly 20 shown in FIG. 3. The same numerals are used in FIG. 4 to depict components previously described. The check valve assembly includes a valve member 128 which, in conjunction with O-ring 130, seals against the seating surface 132, and is biased toward seating engagement by spring 192, which acts between the valve member 128 and the adjustment member, such as check valve stud 194. For any given stud 194, the spring 192 will exert substantially a constant biasing force on the valve member 128, so that the check valve assembly 190, in that sense, is not adjustable. According to the present invention, however, adjustment of the valve assembly 190 is made by selecting one of a group of studs 194 which are identical, except that the base 196 for the pocket 198 varies relative to the end surface 207. In other words, a selected adjustment member 194 having pocket depth between surfaces 207 and 196 of 1.0 centimeters exerts substantially more force upon the valve member 128 than an otherwise identical stud member 194 with a pocket depth of 1.5 centimeters. A service representative for the pump of the present invention thus may maintain a selection of, for example, six studs 194 each having a different pocket depth, and may thereby selectively adjust the biasing force on the valve assembly 190. As still another alternative, the representative may also maintain a selection of different biasing springs 192 which are configured to exert a different biasing force on the valve member for any one of the six studs 194. By combining a reasonable number of studs with a reasonable number of springs, a desired high number of adjustment combinations may be had, so that a desired pump downstream pressure range may be easily obtained by selecting one of the combination setting that will result in the preferred downstream pressure.

Those skilled in the art will appreciate that the sampling pump of the present invention may be ideally suited for withdrawing 0.5 cc bite volumes from an upstream gas line at 5 psi, and for outputting with each pump stroke that volume of gas to a sampling container at an exemplary pressure of 15 psi. Various modifications to the pump will be apparent from the foregoing description, and the pump of the present invention may be designed for utilization with various upstream fluids maintained at different pressure ranges. The pump of the present invention may be used for applications wherein the pump is not withdrawing a sampling fluid from a line, tank, or other source, then outputting fluid to a container. In such another application, the pump may withdraw a small volume of fluid from a source, such as a pressure bottle housing a highly olfactic gas, and discharging that olfactic gas to a natural gas distribution line. In this application, the pump is thus acting as an injection pump to inject a small amount of olfactic gas in the natural gas line to assist in gas leakage detection. Accordingly, it should be understood that the upstream "source" for supplying fluid to the pump of the present invention should be construed to mean any upstream line, tank, or other chamber housing the upstream fluid, and the term "container" that receives the output fluid from the pump should similarly be understood to include not only a conventional sampling container, but also a downstream line or another chamber that receives the downstream fluid.

According to the method of the present invention, the upstream contaminated fluid is filtered by a filter positioned within the pump body, and the same filter cleans fluids entering the pumping chamber and fluids supplied to the actuator unit to drive the pump. The filter may be easily checked and cleaned, if necessary, by unthreading a resealable plug provided in the pump body side port, removing the filter, then re-installing the cleaned filter and plug. Fluid within the pump body may be diverted by a member positioned along the plunger axis between the plunger and the pump body inlet. The fluid pump may be purged by the service technician, if desired, by operating a purge valve that has its seat also within the pump body. To adjust the stroke of the piston, the actuator cap may be removed from the pump actuator body, and a preferred adjustment member having a top surface a selected distance above the upper lace of the piston may be threaded or otherwise secured to an attachment member carried by the piston. The downstream pressure is controlled by a valve member for sealing engagement with the outlet seat positioned within the valve body, and an adjustment member secured to the pump body may be used for selectively controlling the downstream fluid pressure. In a preferred embodiment, an adjustable valve includes a sleeve member secured to the valve body, and an adjustment screw within a threaded passageway in a sleeve member for adjusting force of the biasing member on the valve member. A resealable end cap may be threaded to the sleeve for sealing engaging the sleeve member. Various alternative methods of operating a pump will be apparent to those skilled in the art from the above description.

Additional modifications and alterations to the embodiments and methods described above should now be apparent to one skilled in the art from the foregoing description. Various further modifications may thus be made in accordance with the teachings of the present invention, and the invention is thus not restricted to the preferred embodiments discussed herein and shown in the accompanying drawings. The scope of the invention should thus be understood to include all embodiments within the reasonable scope of the following claims.

What is claimed is:

1. A sampling pump for withdrawing contaminated fluid from a source and outputting fluid to a container, the pump comprising:

a pump body having a central axis, a pump body inlet for fluid-tight communication with the source, the pump body inlet having an inlet axis substantially aligned with the pump body central axis, and a pump body outlet for fluid-tight communication with the container;

a plunger axially reciprocal within the pump body for varying the volume of a fluid receiving chamber within the pump body to receive fluid from the source and discharge fluid to the container during a complete pumping cycle;

a discharge check valve for preventing fluid flow from the container to the fluid receiving chamber;

a pump inlet check valve for preventing fluid flow from the fluid receiving chamber to the pump body inlet;

an operator unit for reciprocating the plunger;

a side body port in the pump body positioned between the pump body inlet and the pump inlet check valve, the side body port extending outward from the central axis of the pump body to an outer surface of the pump body;

a filter removable and insertable through the side body port for filtering fluids passing from the pump body inlet to the fluid receiving chamber;

a diverter member positioned along the pump body central axis and between the plunger and the pump body inlet, the diverter member being removably affixed to the pump body for diverting fluid flow through the filter;

a removable plug for sealing the side body port, such that the plug and filter may be periodically removed from the side body port and repeatedly reinserted into the side body port;

the operating unit powered by fluid pressure to reciprocate the plunger; and a fluid pressurizing line having an inlet positioned between the filter and the pump inlet check valve and an outlet in fluid communication with the operator unit.

2. The sampling fluid pump as defined in claim 1, further comprising:

the filter is a cup-shaped member having a filter axis substantially normal to the pump body central axis.

3. The sampling pump as defined in claim 1, further comprising:

a purge line interconnecting the pump body inlet and the pump body outlet; and a purge valve positioned along the purge line and having a valve member movable within the pump body for selectively controlling fluid flow from the pump body inlet to the pump body outlet.

4. The sampling pump as defined in claim 3, further comprising;

the purge line being contained within the pump body and interconnecting the inlet of the fluid pressurizing line and the pump body outlet; and the discharge check valve is positioned opposite the purge valve with respect to the pump body central axis in alignment with the plunger, the pump body outlet being positioned within the pump body circumferentially between the purge valve and the discharge check valve, and the inlet of the fluid pressurizing line being positioned within the pump body circumferentially between the purge valve and the discharge check valve and opposite the pump body outlet port with respect to the pump body central axis.

5. The sampling pump as defined in claim 4, wherein the discharge check valve comprises:

a valve member for sealing engagement with an outlet valve seat within the valve body;

a biasing member for biasing the valve member into engagement with the outlet valve seat; and an adjustment member removably secured to the pump body and having a stop surface engaged by the biasing member for selectively controlling the spacing between the outlet seat and the stop surface on the adjustment member.

6. A fluid pump for withdrawing fluid from a source and outputting fluid to a container, the pump comprising:

a pump body having a central axis, the pump body having a pump body inlet for fluid-fight communication with the source, a pump body outlet for fluid-tight communication with the container, and a valve port, the pump body inlet having an inlet axis, the pump body outlet having an outlet axis, and the valve port having a valve adjustment axis spaced from both the inlet axis and the outlet axis;

a plunger axially reciprocal within the pump body for varying the volume of a fluid receiving chamber within the pump body to receive fluid from the source and discharge fluid to the container during a complete pumping cycle;

the valve port in the pump body being in fluid communication with both the fluid receiving chamber and the outlet port, the valve port extending outward from the central axis of the pump body to an outer surface of the pump body;

a pump inlet check valve for preventing fluid flow from the fluid receiving chamber to the pump body inlet;

an adjustable discharge check valve for preventing fluid flow from the container to the fluid receiving chamber, the adjustable discharge check valve having a valve member for sealing engagement with a check valve seat within the valve port of the pump body, a biasing member for biasing the valve member into engagement with the check valve seat, and an adjustment member removably secured to the pump body and having a stop surface engaged by the biasing member for selectively controlling the spacing between the check valve seat and the stop surface on the adjustment member, the adjustment member being movable along the valve adjustment axis for adjusting fluid flow through the discharge check valve; and an operator unit for reciprocating the plunger.

7. The fluid pump as defined in claim 6, wherein the adjustment member comprises:
- a sleeve member secured to the valve body and having a threaded passageway therein;
- an adjustment screw within the threaded passageway and axially movable therein by rotation of the adjustment screw relative to the sleeve member; and
- a resealable end cap for sealing engagement with the sleeve member to seal fluids within the adjustable discharge check valve.

8. The fluid pump as defined in claim 6, wherein the adjustable member comprises:
- a check valve stud having a pocket for receiving the biasing member, the stud pocket having a selected depth for controlling the biasing force on the valve member.

9. The fluid pump as defined in claim 6, further comprising:
- a filter for filtering fluids passing from the fluid inlet to the fluid receiving chamber;
- the pump body fluid inlet having an inlet axis substantially aligned with the pump body central axis; and
- a diverter member positioned along the plunger axis and between the plunger and the pump body fluid inlet for diverting fluid flow through the filter.

10. The fluid pump as defined in claim 9, further comprising:
- the operator unit is powered by fluid pressure to reciprocate the plunger; and
- a fluid pressurizing line having an inlet positioned between the filter and the pump inlet check valve and an outlet in fluid communication with the operator unit.

11. The fluid pump as defined in claim 10, further comprising:
- a purge line interconnecting the pump body inlet and the pump body outlet;
- a purge valve positioned along the purge line and having a valve member movable within the pump body for selectively controlling fluid flow from the inlet of the pressurizing line to the pump body outlet; and
- the discharge check valve is positioned opposite the purge valve with respect to the pump body central axis in alignment with the plunger, the pump body outlet being positioned within the pump body circumferentially between the purge valve and the discharge check valve, and the inlet of the fluid pressurizing line being positioned within the pump body circumferentially between the purge valve and the discharge check valve and opposite the pump body outlet port with respect to the pump body central axis.

12. A pump for withdrawing fluid from a source and outputting fluid to a container, the pump comprising:
- a pump body having a central axis, the pump body having a pump body inlet port for fluid-tight communication with the source and a pump body outlet port for fluid-tight communication with the container, the pump body further including a check valve port, a purge valve port, and an operator pressurizing line port, the pump body including therein a purge line for fluid communication between the pump body inlet port and the pump body outlet port;
- the pump body outlet port being circumferentially positioned on the pump body between the check valve port and the purge valve port, and the operator pressurizing line port being circumferentially positioned on the valve body between the check valve port and the purge valve port and circumferentially opposite the pump body outlet port;
- a plunger axially reciprocal within the pump body for varying the volume of a fluid receiving chamber within the pump body to receive fluid from the source and discharge fluid to the container during a complete pumping cycle;
- a discharge check valve within the check valve port for preventing fluid flow from the container to the fluid receiving chamber;
- a pump inlet check valve for preventing fluid flow from the fluid receiving chamber to the pump body inlet;
- a purge valve positioned within the purge valve port and along the purge line, the purge valve having a valve member movable within the pump body for selectively controlling fluid flow from the pump body inlet port to the pump body outlet port;
- a fluid pressurizing line having an inlet positioned hydraulically between the pump body inlet port and the pump inlet check valve and an outlet in fluid communication with the operator unit, the fluid pressurizing line being in fluid communication with the operator pressurizing line port; and
- an operator unit for reciprocating the plunger, the operator unit including a fluid-pressure responsive sealing member axially interconnected with the plunger for reciprocating the plunger in response to movement of the sealing member.

13. The pump as defined in claim 12, further comprising:
- a cup-shaped filter for filtering fluids passing from the pump body inlet to both the fluid receiving chamber and the operator unit.

14. The pump as defined in claim 12, wherein the outlet check valve comprises:
- a valve member for sealing engagement with an outlet valve seat within the valve body;
- a biasing member for biasing the valve member into engagement with the outlet valve seat; and
- an adjustment member removably secured to the pump body and having a stop surface engaged by the biasing element for selectively controlling the spacing between the outlet seat and the stop surface on the adjustment member.

15. A method of operating a pump for withdrawing fluid from a source and outputting fluid to a container, the pump having a central axis, the pump body having a pump body inlet for fluid communication with the source and the pump body outlet for fluid communication with the container, the pump body inlet having an inlet axis, and the pump body outlet having an outlet axis, the pump including a plunger reciprocal within the pump body for varying the volume of a fluid receiving chamber to receive fluid from the source and discharge fluid to the container during a pumping cycle, the method comprising:
- preventing fluid flow from the fluid receiving chamber to the pump body inlet;
- forming a valve port in the pump body in fluid communication with both the fluid receiving chamber and the pump body outlet and extending outward from the central axis of the pump body to an outer surface of the pump body;
- positioning an adjustable discharge check valve within the valve port for preventing fluid flow from the container to the fluid receiving chamber;

movably positioning a valve element within the discharge check valve for engagement with a valve seat on the pump body;

positioning an adjustment member movable with respect to the pump body; positioning a biasing spring between the adjustment member and the valve element; and moving the adjustment member to alter the biasing force of the biasing spring and thereby adjust fluid flow through the discharge check valve without disconnecting fluid lines interconnected with the pump body.

16. The method of operating a pump as defined in claim 15, further comprising:

positioning an outlet of the fluid pressurizing line in fluid communication with a pump operating unit; and powering the operating unit with the source fluid to move the plunger;

providing a purge line within the pump body interconnecting the pump inlet port and the pump outlet port;

providing a purge valve along the purge line; and selectively controlling the purge valve to control fluid flow from the pump body inlet to the pump body outlet.

17. The method of operating a pump as defined in claim 15, further comprising:

forming the valve port about a valve adjustment axis spaced from both the pump inlet and the pump outlet;

positioning a filter within the valve body to filter fluid passing from the pump body inlet to the fluid receiving chamber; and periodically removing the plug positioned within the side body port, removing the filter from the side body port, re-inserting the filter in the pump body through the side body port, and re-installing the plug in the side body port.

18. The method of operating a pump as defined in claim 16, further comprising:

positioning a diverter along the pump body central axis and between the plunger and the pump body inlet port for diverting fluid flow through the filter.

* * * * *

UNITED STATES PATENT AND TRADEMARK OFFICE
CERTIFICATE OF CORRECTION

PATENT NO. : 5,522,708
DATED : June 4, 1996
INVENTOR(S) : Spencer M. Nimberger

It is certified that error appears in the above-indentified patent and that said Letters Patent is hereby corrected as shown below:

In column 4, line 19, delete "pump assembly" before "pump 10".

In column 4, line 23, delete "pump assembly" before "pump 10".

In column 4, line 40, delete "pump assembly" before "pump 10".

In column 12, line 31, delete ";" after "passing".

In column 14, line 16, change "16" to --17--.

Signed and Sealed this

Tenth Day of September, 1996

Attest:

BRUCE LEHMAN

*Attesting Officer*      Commissioner of Patents and Trademarks